United States Patent
Eichner et al.

(10) Patent No.: US 9,377,381 B2
(45) Date of Patent: Jun. 28, 2016

(54) DEVICE FOR DETECTING SOLIDS

(75) Inventors: Harald Eichner, Schwanau-Ottenheim (DE); Michael Huck, Buehl (DE)

(73) Assignee: Kaba Gallenschuetz GmbH, Buehl (DE)

(*) Notice: Subject to any disclaimer, the term of this patent is extended or adjusted under 35 U.S.C. 154(b) by 341 days.

(21) Appl. No.: 14/111,273

(22) PCT Filed: Apr. 5, 2012

(86) PCT No.: PCT/DE2012/100095
§ 371 (c)(1),
(2), (4) Date: Oct. 11, 2013

(87) PCT Pub. No.: WO2012/139564
PCT Pub. Date: Oct. 18, 2012

(65) Prior Publication Data
US 2014/0102174 A1    Apr. 17, 2014

(30) Foreign Application Priority Data

Apr. 15, 2011  (DE) .......................... 10 2011 002 097

(51) Int. Cl.
| | | |
|---|---|---|
| *G01N 1/22* | (2006.01) | |
| *G01N 15/00* | (2006.01) | |
| *G01N 1/00* | (2006.01) | |
| *G01N 1/02* | (2006.01) | |

(52) U.S. Cl.
CPC .............. *G01N 1/2214* (2013.01); *G01N 15/00* (2013.01); *G01N 2001/002* (2013.01); *G01N 2001/024* (2013.01); *G01N 2015/0019* (2013.01)

(58) Field of Classification Search
CPC ................. G01N 1/2214; G01N 2015/0019; G01N 2001/002
See application file for complete search history.

(56) References Cited

U.S. PATENT DOCUMENTS

| 4,819,477 A | 4/1989 | Fisher et al. |
| 4,987,767 A | 1/1991 | Corrigan et al. |

(Continued)

FOREIGN PATENT DOCUMENTS

| DE | 690 30 686 T2 | 9/1997 |
| DE | 690 33 217 T2 | 12/1999 |

(Continued)

OTHER PUBLICATIONS

International Search Report of PCT/DE2012/100095, dated Jul. 23, 2012.

*Primary Examiner* — Paul West
(74) *Attorney, Agent, or Firm* — Collard & Roe, P.C.

(57) ABSTRACT

Secure areas, such as at airports or other security-critical facilities, are entered from freely accessible areas, often by means of access locks. This bottleneck, which is present in any case, is used to check for substances of concern, such as drugs or explosive materials. In the case of solids, as is known, particles extracted from the access lock and retained in a screen are vaporized and the vapor is examined. Several of the screens are arranged on rotatable carrying disks and undergo consecutively the steps of vaporization and analysis. The aim of the invention is to make known methods more efficient in order to increase the throughput through such access locks. The aim is achieved by a device for which available heating and extraction elements are assigned to multiple rotational positions of the carrying disks, whereby adjacent rotational positions lie apart from each other by only half the distance of two screens.

15 Claims, 3 Drawing Sheets

(56) References Cited

U.S. PATENT DOCUMENTS

Figure 1:
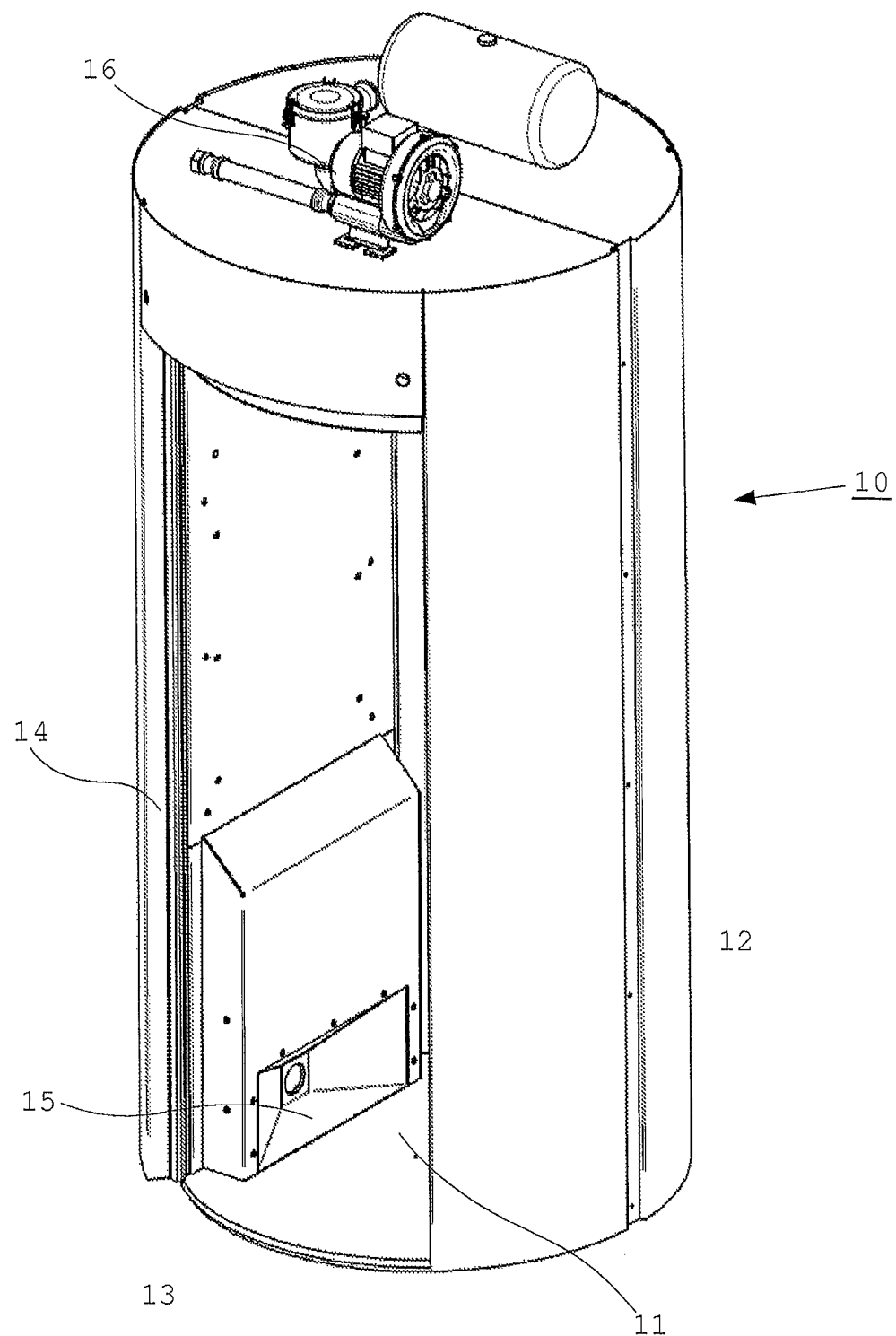

| | | |
|---|---|---|
| 5,109,691 A | 5/1992 | Corrigan et al. |
| 2002/0106804 A1* | 8/2002 | Tanaka .................. G01N 35/10 436/54 |
| 2009/0044641 A1 | 2/2009 | Konduri et al. |

FOREIGN PATENT DOCUMENTS

| | | |
|---|---|---|
| EP | 0 236 047 A2 | 9/1987 |
| EP | 0 447 158 A2 | 9/1991 |
| EP | 0 905 501 A2 | 3/1999 |
| GB | 2 176 008 A | 12/1986 |

* cited by examiner

DEVICE FOR DETECTING SOLIDS

CROSS REFERENCE TO RELATED APPLICATIONS

This application is the National Stage of PCT/DE2012/100095 filed on Apr. 5, 2012, which claims priority under 35 U.S.C. §119 of German Application No. 10 2011 002 097.7 filed on Apr. 15, 2011, the disclosure of which is incorporated by reference. The international application under PCT article 21(2) was not published in English.

The present invention relates to an apparatus for detection of solids, particularly of explosive substances or drugs, comprising a carrier disk on which multiple screens are disposed with rotation symmetry, whereby an intake channel for drawing ambient air in through the screen, in each instance, is assigned to the screens in a first rotational position, and a first heating element for vaporization of particles of the solids to be detected, which particles were collected in the screen, in each instance, during intake, and an intake channel connected with an analysis device, for drawing off the vaporized particles, are assigned to the screens in a second rotational position.

Such an apparatus is already previously known from EP 0 447 158 A2. A carrier disk having a total of four screens is moved between different rotational positions, in this connection, whereby one screen is in engagement with every device to be used, in one rotational position, in each instance.

Further solutions from the state of the art, for example according to DE 690 30 686 T2. having six screens in six rotational positions, and according to GB 2 176 008 A, having three positions that have sample carriers, in each instance, have a similar structure.

A corresponding solution is also previously known from DE 690 33 217 T2. This involves a detection system for explosive substances, in which air is first drawn off from a spatial volume to be examined, and passed through a metal screen. Any solid particles that are drawn away with the air are captured by the metal screen, which is disposed on a rotating disk. Each metal screen passes through three rotational positions of the rotating disk, one after the other, whereby in a first rotational position, drawing off takes place out of the spatial volume to be monitored. In a second rotational position, the metal screen is heated using a heating element, so that the particles that settle on the metal screen are vaporized. The resulting vapor is passed to an analysis device that is able to characterize the particles contained in the vapor and can detect any substances being sought, such as explosive substances or drugs or the like. In a third position, further heating of the metal screen takes place, and the residual particles remaining in the metal screen, which have now been carbonized as a result of this further heating, are suctioned away.

A test for such solids usually takes place when passing from a non-secure to a secure area, as this takes place, for example, at airports. It is fundamentally possible, in this connection, to subject both objects and persons to such a test. In both cases, the object to be investigated is introduced into an air lock, to which an air stream is applied, which is drawn off by the apparatus described above. Until the end of the analysis, it must be ensured, in this connection, that the person or object remains identifiable at all times, so that the person or object must be detained during the analysis.

This is easily possible, in the case of persons, in that the person enters into a spatial volume, for example in the form of an access lock, for the examination, that this lock is closed after the person enters it, and opened again only after the analysis is completed. According to the solution according to the state of the art, multiple screens are already disposed on the rotating disk for this purpose, with rotation symmetry, so that a complete revolution of the disk and complete passing through all three rotational positions is not necessary to finish processing a person. The third rotational position can be performed by the metal screen in question also during an interim step or at the same time, while another screen is being impacted.

Against this background, the present invention is based on the task of improving the efficiency of the known apparatus for detection of solids, and of increasing the capacity utilization and efficient utilization of the components used.

This is accomplished by means of an apparatus for detection of solids according to the characteristics of the main claim. Further embodiments of this apparatus can be derived from the dependent claims.

According to the invention, a rotating carrier disk is also present, on which a plurality of screens is disposed with rotation symmetry. Any suitable material can be used for the production of the screens, for example, metal screens, ceramic screens, and—to the extent that they are sufficiently heat-resistant—plastic screens can also be used. A preferred embodiment of the carrier disk provides for a total of three metal screens. In this connection, in a first rotational position of the carrier disk, one screen is in engagement with an intake channel through which ambient air is drawn in through the screen. Subsequently, the screen in question is brought into a second rotational position, where a first heating element is provided for vaporization of the particles captured in the screen. The particles vaporized in this manner are brought through an aspirator channel, in the direction of an analysis device that examines the vaporized particles to determine whether they are critical particles, for example particles of explosive substances or drugs.

An angle $\alpha$ lies between the first and the second rotational position, which angle is selected in such a manner that the angle distance between the two screens amounts to an even-numbered multiple of this angle $\alpha$. In this way, when the carrier disk is rotated by one rotational position, in each instance, a switch takes place, at a rotational position, between a screen and a blind spot that lies in between. The devices that belong to each rotational position are therefore put into operation, in each instance, at every other change in rotational position of the carrier disk. By means of a corresponding configuration of the devices provided at the rotational positions, in each instance, it can be ensured that these are not put into operation at the blind spots, so that the related energy can be saved. Vice versa, it is also possible to eliminate a complicated control for recognizing a blind spot or a screen that is not needed at a specific time.

For cleaning of the screens, which can still be impacted by residual particles, a second heating element can be provided at a third rotational position, which element carbonizes the residual particles. Within the scope of the first heating, during which vaporization of the particles is supposed to be brought about, the screen is heated to approximately 180° C., while significantly greater heat, in the range above 300° C., is required within the scope of carbonization. Accordingly, a first heat radiator can be disposed at the second rotational position, which can possess a heat output of approximately 300 watts, for example. Then, a second heating element in the form of a heat radiator is then disposed at the third rotational position, which possesses double the output, in other words preferably approximately 600 watts.

To improve the efficiency, however, it is also possible to work with other heating methods. For example, it is particularly provided that the heating elements are induction coils, whereby induction loops are accordingly assigned to the screens, which loops are able to convert the current induced by the induction coils in the region of the screens into heat. These induction loops are preferably woven into the screen, in this connection, in order to allow ideal heat transfer to the material of the screen.

A particularly preferred embodiment of the invention provides for producing the screens from a ferromagnetic material, as metal screens, so that these metal screens as a whole act as an induction loop.

These embodiments can be developed further in that the third rotational position with the second heating element is offset from the second rotational position by an odd multiple of the angle $\alpha$. In this way, it is guaranteed that a screen is present, in each instance, at a specific point in time only at one of the two rotational positions provided with a heating element. If a screen is now present at the second rotational position, a current generator that is connected with the induction coil is operated at a lower output, while the output is increased when a screen is situated at the third rotational position.

In this connection, it is practical if a material that does not react with the induction coil, in other words a non-ferromagnetic material, is disposed at the blind spots. This can be done, for one thing, in that the entire carrier disk is produced from a non-ferromagnetic material, for example an austenitic material. Alternatively, however, a shutter similar in shape to the screens can be provided in the region of the blind spots, which shutters are also attached to the carrier disk with identical, raised frames, if necessary. Preferably, these blind spots are also situated with rotation symmetry, in each instance, distributed over the circumference of the carrier disk, centered between the screens.

In a further development of the apparatus, a fourth rotational position can also be present, which has an aspiration apparatus for drawing off carbonized particle residues. For this purpose, a second aspiration channel is present, which also could be joined, for example, with a central aspiration system that also provides the aspiration of the air stream out of the spatial volume to be monitored.

In order to be able to perform the aspiration despite the rotating carrier disk, it is necessary that the intake and aspiration channels, respectively, can be contacted with the carrier disk in every rotational position, whereby after the work step, in each instance, has been carried out, release from the carrier disk takes place again. This can take place, for example, in that a double-wall folded bellows is assigned to the intake and aspiration channels, respectively, which bellows has a connector in the end position, on the side that contacts the carrier disk, which seals off the disk. To the extent that a frame is provided around the screens or the shutters that might be present, this frame can also be contacted using the connector.

Contacting by means of the connector, which can be moved out using the folded bellows and brought into contact with the carrier disk or the frame, respectively, takes place by way of applying an excess pressure in the double-wall folded bellows, which unfolds as the result of this excess pressure and thereby straightens up in the direction of the carrier disk. As a result, a friction fit occurs between the connector and the carrier disk or frame, respectively, which fit can be released again by lowering the excess pressure, if necessary also by applying a partial vacuum to the double-wall folded bellows. In this connection, the excess pressure is applied between the two walls of the folded bellows, while the interior of the folded bellows forms an air channel provided for intake or aspiration. Of course, only the suction pressure is applied to this inner channel, during this process.

The position control of the carrier disk takes place by way of a controlled drive, whereby this is an electrical drive, for example. In this connection, this drive can drive a gear wheel that engages into a corresponding, gear-wheel-like knurling of the carrier disk in the region of its circumference. However, other possibilities of the drive of the carrier disk are possible, and are explicitly also covered by the invention.

The spatial volume from which the air stream to be examined is drawn off can be an access lock, for example, which is closed off completely, in air-tight manner, to a great extent. Using a pump, an air stream is applied by way of air nozzles in the ceiling region of such an access lock, which runs through the access lock and the spatial volume enclosed by it essentially from top to bottom, and can be viewed as a type of air shower, in this regard. In the floor region, aspiration by way of an aspiration funnel takes place, which ends in the aspiration channel to which the screen is applied.

To further increase the efficiency of such an arrangement, a second carrier disk, which functions synchronously, offset by a rotational position, can be provided, which disk is assigned to a second access lock with a second spatial volume. In this way, it is possible to use the analysis device and also further components, such as the heating system, for example, simultaneously at multiple positions, and thereby to clearly reduce the idle times of the individual components.

The apparatus for detection of solids will be explained in greater detail below, using an exemplary embodiment.

Figure 2:
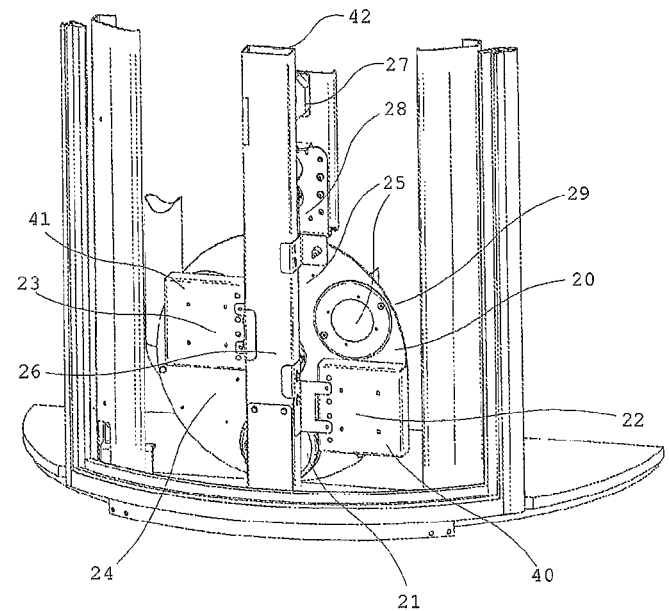
Figure 3:
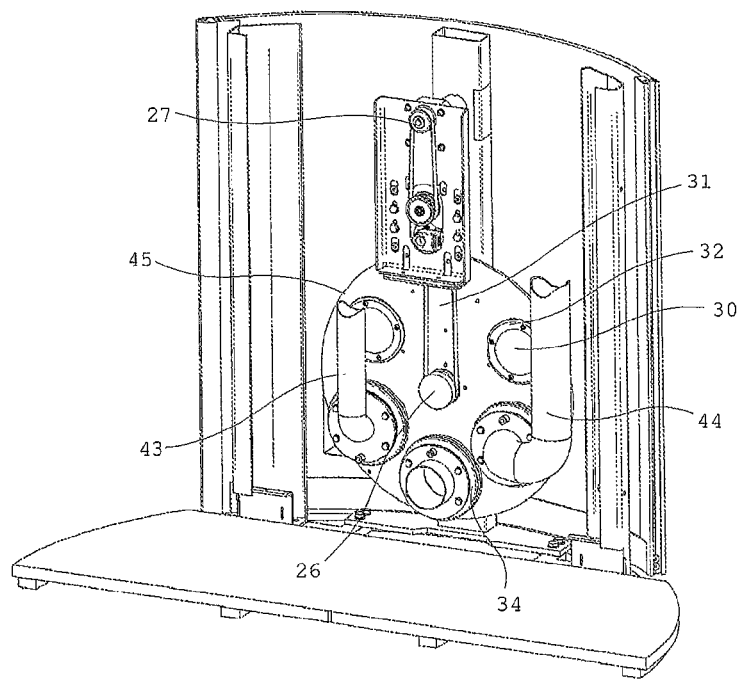
Figure 4A:
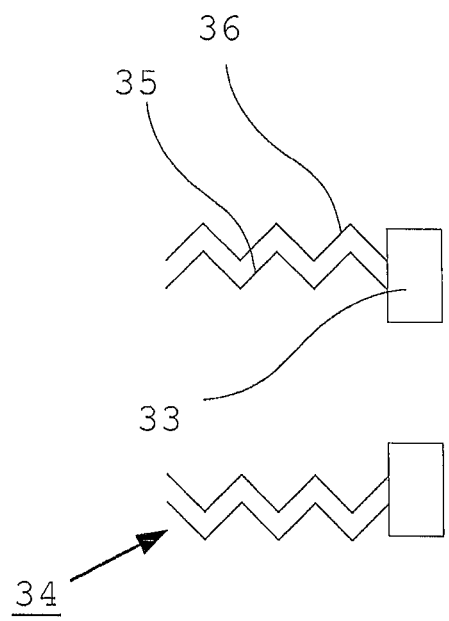
Figure 4B:
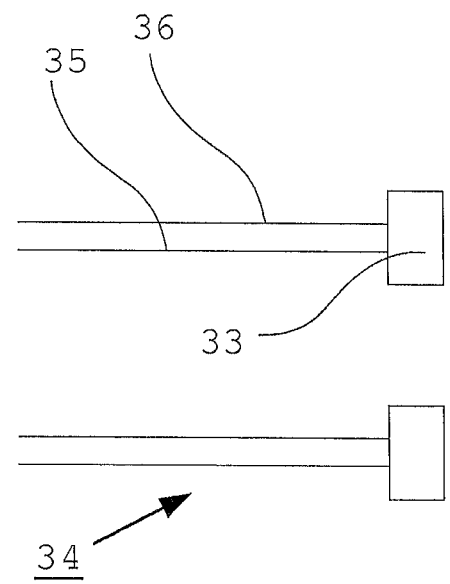

The figures show:

FIG. 1 an access lock with an apparatus according to the invention, in a perspective representation, at a slant from above, FIG. 2 the apparatus according to the invention, in a view from outside of the spatial volume to be monitored, in a perspective view at a slant from above, with the cover removed, FIG. 3 the apparatus according to FIG. 2 in a perspective view from within the spatial volume to be monitored, at a slant from above, with the cover removed, FIG. 4a a double-wall folded bellows for contacting the intake or aspiration channel with the carrier disk, in a sectional representation, without pressure applied between the double walls, and FIG. 4b the folded bellows according to FIG. 4a in a sectional representation, with pressure applied between the double walls.

FIG. 1 shows an access lock 10 that separates a secure area 12 from a non-secure area 13. A person passing from the non-secure area 13 into the secure area 12 must pass through a spatial volume 11 for this purpose, which volume is enclosed by the said access lock 10. For this purpose, the person first enters the spatial volume 11 from the non-secure area 13, and after that, the door 14 of the access lock 10 is closed. At this point in time, a second door on the side of the secure area 12 is also closed, so that the person is locked into the spatial volume 11 at this point in time. Using a pump 16, an air stream is generated in the spatial volume 11, which stream essentially flows from the ceiling of the access lock 10 in the direction of its floor, and is drawn off by way of an intake funnel 15. The intake funnel 15 is part of a cover of the apparatus according to the invention, by way of which the person located in the access lock 10 is investigated with regard to carrying suspicious solids, particularly explosive substances or drugs, as follows.

Within the housing described above, there is the arrangement shown in FIG. 2, which is shown without any housing part, for a better understanding. Essentially, this is a carrier disk 20 on which a plurality of metal screens 30 are disposed. Using the carrier disk 20, the metal screens 30 are moved between different rotational positions. In this connection, the metal screens 30 are disposed on the carrier disk 20 in such a manner that a metal screen 30 alternates with a blind spot 11, in each instance. In the present example, a total of three metal screens 30 are provided on the carrier disk 20, so that a total of three blind spots 31 are present between these metal screens 30. The carrier disk 20 can be turned using a drive 27 that moves a gear wheel 28 that engages into a knurling 29 of the carrier disk 20. From one rotational position 21 to 25 to the next, the carrier disk 20 moves over an angle α during this process, whereby this also involves the angle distance between a metal screen and an adjacent blind spot, in each instance. By means of the change from one rotational position 21 to 25 to the next, alternation between a blind spot 31 and a metal screen 30 takes place at a rotational position 21 to 25 being considered, in each instance.

In a first rotational position 21, aspiration as described above in connection with FIG. 1 takes place. When the air is drawn off from the spatial volume 11 to be monitored, this aspirated air passes through a metal screen 30, so that any particles present in the air stream are caught in the metal screen 30. After this impact of particles to be detected on the metal screen 30, rotation of the carrier disk 20 into a second rotational position takes place. Once the metal screen 30 arrives at this second rotational position 22, it comes into engagement with a first heating element 40, which brings about heating of the metal screen 30. This first heating element can be an induction coil, for example, which excites an induction loop woven into the metal screen 30 and thereby heats the metal screen 30. The resulting vapor is drawn, using a first aspiration channel 43, to an analysis device 45 in which an analysis of the particles that have been vaporized in this manner, if applicable, takes place.

In the present example, the metal screen 30 being considered in the following passes through two idle positions 25 before it is brought into the third rotational position 23. There, the metal screen 30 comes into engagement with a second heating element 41, which brings about clearly stronger heating of the metal screen and thereby causes carbonization of any particles still present on the metal screen 30. In a fourth rotational position, aspiration of any carbonized particles still present on the metal screen 30 finally takes place.

Because of the use of blind spots at every other rotational position, these rotational positions are put out of operation, in each instance. As a result, intake and aspiration channels that are applied to the blind spots are closed, and suction is prevented. Furthermore, the shutters used at the blind spots 31 can be shutters composed of a non-ferromagnetic material, for example an austenitic metal, which does not result in any heating when the magnetization of an induction coil is applied, so that in this manner the energy consumption is reduced, by means of the heating that is prevented as a result.

FIG. 3 shows the same arrangement as FIG. 2, seen from the inside of the spatial volume 11. As a result, the drive 27 that puts the carrier disk 20 into rotation about its axis of rotation 26, using its knurling 29, can be clearly seen. The aspiration channels 43 and 44, which are brought into contact with the carrier disk 20 in the region of this disk, using folded bellows 34, can also be clearly seen.

This is shown in greater detail in FIGS. 4a and 4b. The folded bellows 34 are structured with a double wall, in other words have an inner wall 35 and an outer wall 36. Connectors 33 are affixed at the ends of these folded bellows 34, which connectors can enter into contact with the carrier disk 20 or a frame 32 possibly disposed on the metal screen 30, forming a seal. If the carrier disk 20 now reaches a rotational position 21 to 25 and comes to a stop, the space between the inner wall 35 and the outer wall 36 has an excess pressure applied to it. As a result, the situation of the folded bellows 34 changes from the state of FIG. 4a to the state of FIG. 4b. Because of the excess pressure between inner wall 35 and outer wall 36, the folded bellows 34 is expanded and thereby moves in the direction of the carrier disk 20. In this connection, the movement path is limited by the connector 33, which cannot move any further after making contact with the carrier disk 20. Aspiration or intake of the air can then take place between the double walls, independent of the prevailing excess pressure between inner wall 35 and outer wall 36. Before the carrier disk 20 is turned further, either the excess pressure between the two walls of the folded bellows 34 can be lowered, or it can actually be converted to a partial vacuum, so that the folded bellows is returned to the state as shown in FIG. 4a.

REFERENCE SYMBOL LIST 10 access lock
11 spatial volume
12 secure area
13 non-secure area
14 door
15 intake funnel
16 pump
20 carrier disk
21 first rotational position
22 second rotational position
23 third rotational position
24 fourth rotational position
25 idle position
26 axis of rotation
27 drive
28 gear wheel
29 knurling
30 metal screen
31 blind spot
32 frame
33 connector
34 folded bellows
35 inner wall
36 outer wall
40 first heating element
41 second heating element
42 intake channel
43 first aspirator channel
44 second aspirator channel
45 analysis device

The invention claimed is:

1. An apparatus for detection of solids, comprising a carrier disk on which multiple screens are disposed with rotation symmetry, wherein an intake channel for drawing ambient air in through the screen, in each instance, is assigned to the screens in a first rotational position, and a first heating element for vaporization of particles of the solids to be detected, which particles were collected in the screen, in each instance, during intake, and a first aspiration channel connected with an analysis device, for drawing off the vaporized particles, are assigned to the screens in a second rotational position, wherein the angle distance between two adjacent screens of the carrier disk amounts to an even-numbered multiple of an angle α, which the carrier disk passes through during the transition from one rotational position of the carrier disk to an adjacent rotational position, and wherein the carrier disk is structured with rotation symmetry, in such a manner that as the result of rotation of the carrier disk by the angle α, from one rotational position to the next, a switch from a screen to a blind spot, in each instance, or vice versa takes place at a rotational position, so that the intake and first aspiration channels are closed off by the blind spots in every other rotational position.

2. The apparatus according to claim 1, wherein in a third rotational position, a second heating element for carbonization of any particles still present on the screen is assigned to the screens.

3. The apparatus according to claim 2, wherein the heating elements are heat radiators, whereby the second heating element possesses a greater output than the output of the first heating element (40).

4. The apparatus according to claim 2, wherein the heating elements are induction coils, wherein an induction loop is assigned to the screens, in each instance.

5. The apparatus according to claim 4, wherein the third rotational position is offset relative to the second rotational position by an odd multiple of the angle α, and wherein the induction coils are supplied by a generator that is switched to a higher output whenever a screen is situated at the third rotational position.

6. The apparatus according to claim 2, wherein the heating elements are induction coils and wherein the screens are metal screens functioning as induction loops.

7. The apparatus according to claim 2, wherein in a fourth rotational position, an aspiration apparatus for drawing off carbonized particle residues by way of a second aspiration channel is assigned to the screens.

8. The apparatus according to claim 7, wherein a channel selected from the group consisting of the intake channels and the first and second aspiration channels, respectively, in each instance, is assigned to the screens, at least in the first, second, and fourth rotational position (21, 22, 24), which channel contacts the carrier disk (20) around the screen, in each instance, sealing it, and the carrier disk is released again before the rotational position, in each instance, is departed from.

9. The apparatus according to claim 8, wherein the channel selected from the group consisting of the intake channels and the first and second aspiration channels, respectively, comprises a double-wall folded bellows, in each instance, and has a connector, in the end position, that contacts the carrier disk around the screen, forming a seal, wherein the folded bellows can have an excess pressure applied to it for contacting of the carrier disk, and a partial vacuum applied to it for releasing the carrier disk.

10. The apparatus according to claim 1, wherein a shutter is provided at the blind spots on the carrier disk, in each instance, between two screens, in each instance, which shutter is similar in shape to the screens.

11. The apparatus according to claim 10, wherein shutters and screens are attached to the carrier disk by identical, raised frames.

12. The apparatus according to claim 10, wherein the shutters are composed of a non-magnetic material.

13. The apparatus according to claim 1, wherein the carrier disk has knurling along its outer circumference, and is driven by a gear wheel connected with an electrical drive, which engages into the knurling.

14. The apparatus according to claim 1, wherein each intake channel opens into a closed spatial volume.

15. The apparatus according to claim 14, wherein a second carrier disk, which functions synchronously, offset by a rotational position, is provided, the screens of which disk have ambient air applied to them by way of an intake pipe that opens into a second spatial volume.

* * * * *